United States Patent
Kawasaki et al.

[11] Patent Number: 5,486,194
[45] Date of Patent: Jan. 23, 1996

[54] COMPRESSIVE HEMOSTATIC BELT

[75] Inventors: Atsuko Kawasaki, Akashi; Takefumi Nakashita, Kobe; Yoshiharu Inui, Takarazuka; Toshimichi Shirouzu, Akashi, all of Japan

[73] Assignee: Sumitomo Rubber Industries, Ltd., Kobe, Japan

[21] Appl. No.: 160,214

[22] Filed: Dec. 2, 1993

[30] Foreign Application Priority Data

| Dec. 4, 1992 | [JP] | Japan | 4-325049 |
| Aug. 4, 1993 | [JP] | Japan | 5-193233 |
| Aug. 4, 1993 | [JP] | Japan | 5-193234 |
| Aug. 4, 1993 | [JP] | Japan | 5-193235 |
| Aug. 17, 1993 | [JP] | Japan | 5-202450 |
| Oct. 4, 1993 | [JP] | Japan | 5-247647 |

[51] Int. Cl.[6] ................................ A61B 17/12
[52] U.S. Cl. ........................ 606/203; 602/53; 602/62
[58] Field of Search ................... 606/203, 202; 602/62, 67, 61, 53; 128/118.1, 96.1

[56] References Cited

U.S. PATENT DOCUMENTS

| 3,587,584 | 6/1971 | Keller . | |
| 3,954,109 | 5/1976 | Patel . | |
| 4,224,945 | 9/1980 | Cohen . | |
| 5,139,512 | 8/1992 | Dreiling et al. | 606/203 X |

FOREIGN PATENT DOCUMENTS

| 0462088A2 | 12/1991 | European Pat. Off. . |
| 0514026A2 | 11/1992 | European Pat. Off. . |
| 0554602A1 | 8/1993 | European Pat. Off. . |
| 2323115 | 1/1974 | Germany . |
| 4012974A1 | 10/1991 | Germany . |
| 58-48293 | 4/1977 | Japan . |

*Primary Examiner*—Michael H. Thaler
*Attorney, Agent, or Firm*—Nikaido, Marmelstein, Murray & Oram

[57] ABSTRACT

This invention relates to a compressive hemostatic belt wherein a cup-shaped rigid case is attached by an attaching device to a predetermined position on a band made of non-stretchable or low-stretchable fiber, nonwoven fabric or film, and a balloon adapted to be inflated by being filled with fluid is received in the rigid case. Preferably, at least the portion of the band which corresponds to the leg when the band is wrapped around the body is shaped in curve form. Buckles may be attached to the opposite ends of the band and a buckle attaching plate may be attached to the rigid case. One end of the band may be provided with projections so that when the band is wrapped around the body, the other end of the band is thrusted on the projections to fix the band in position. If the band is made of adhesive material, more reliable fixing can be achieved. A check valve adapted to prevent fluid from flowing back from the balloon may be removably connected to the balloon to provide for reuse of the check valve.

11 Claims, 13 Drawing Sheets

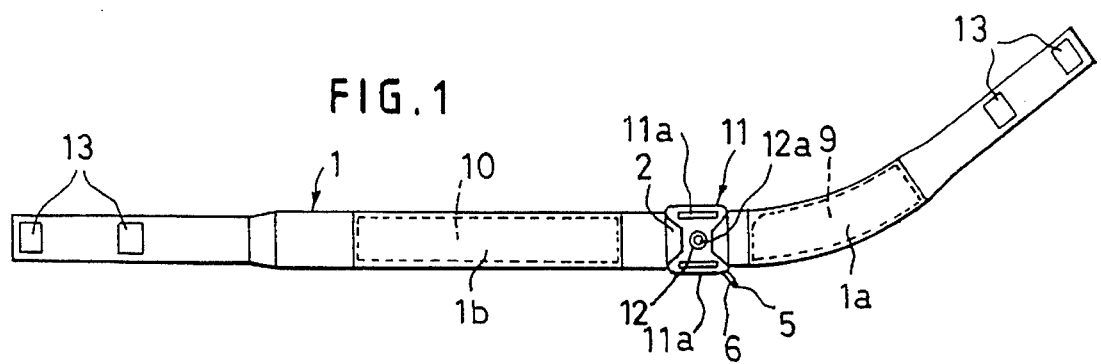
FIG.1
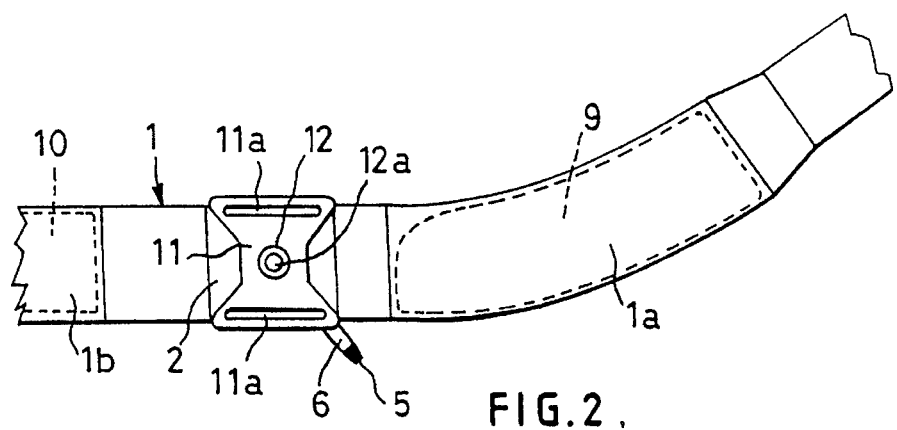
FIG.2.
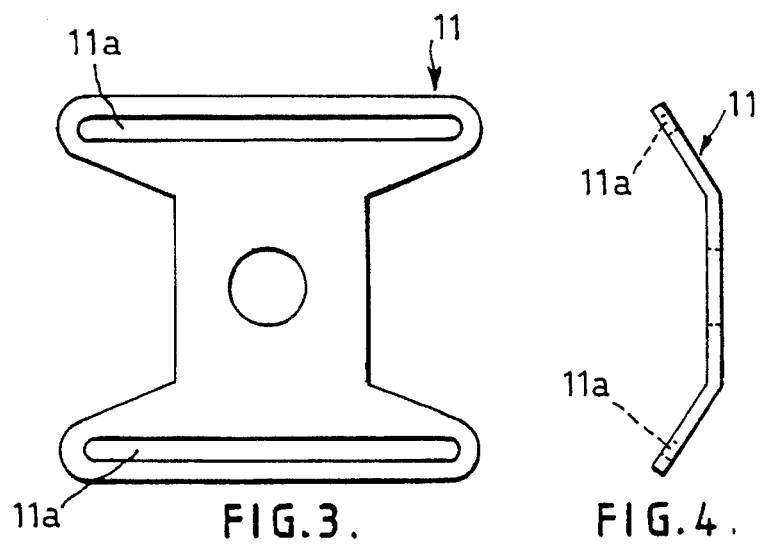
FIG.3.
FIG.4.

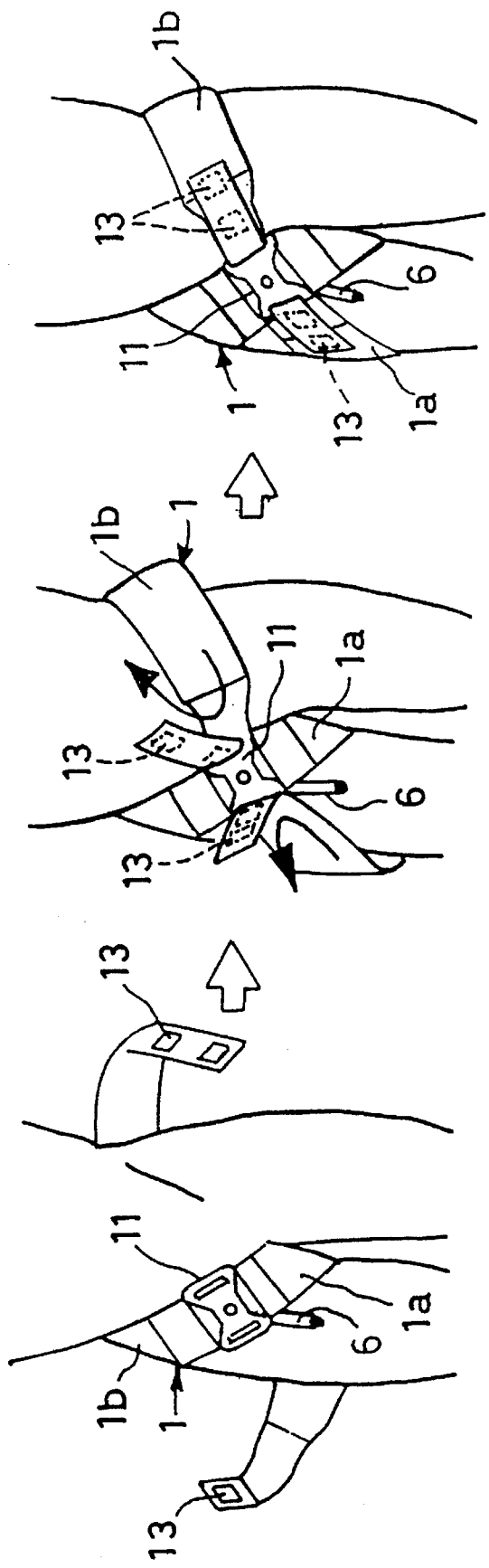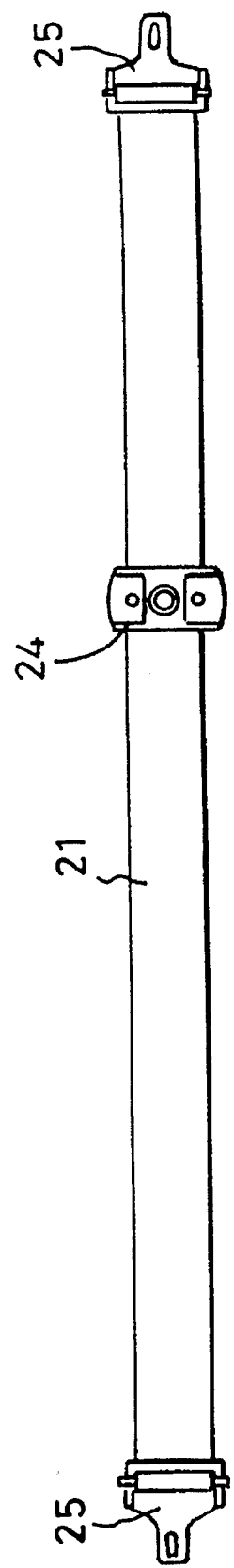

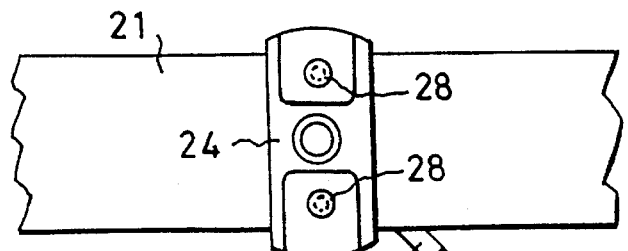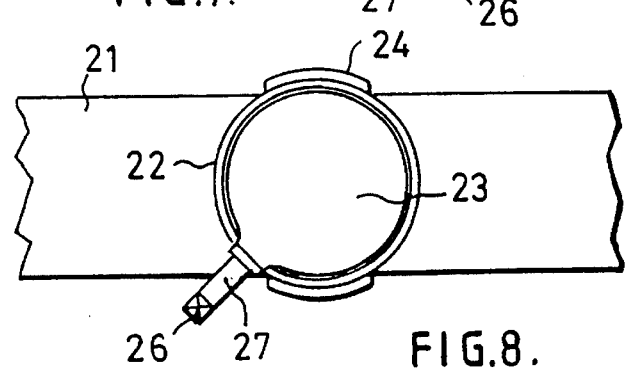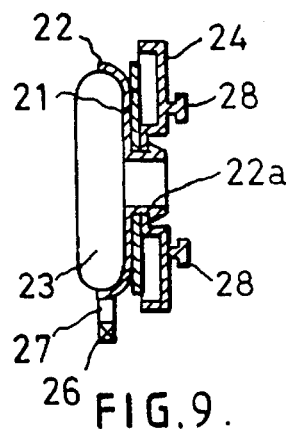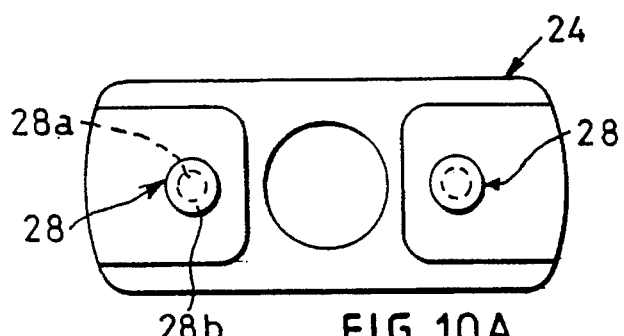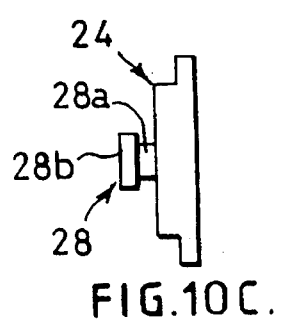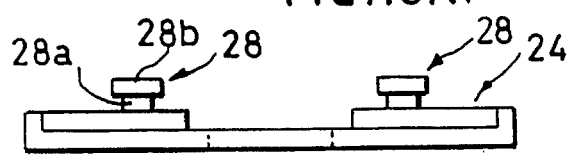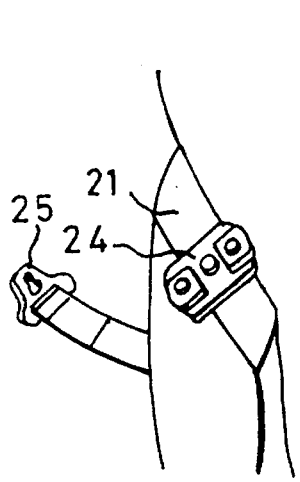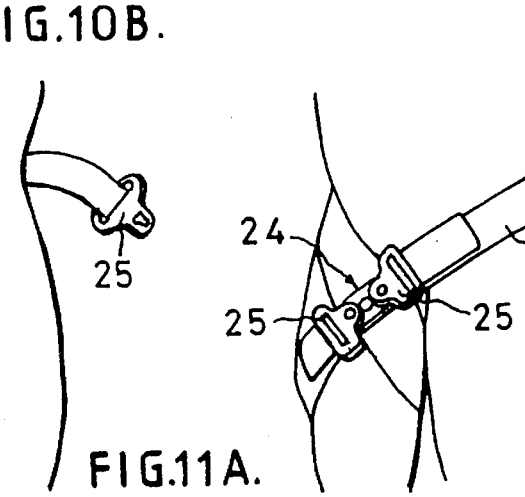

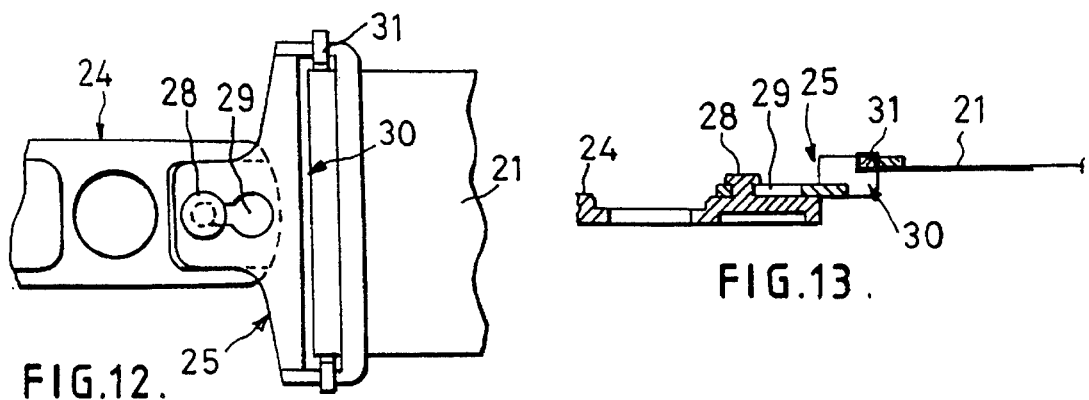
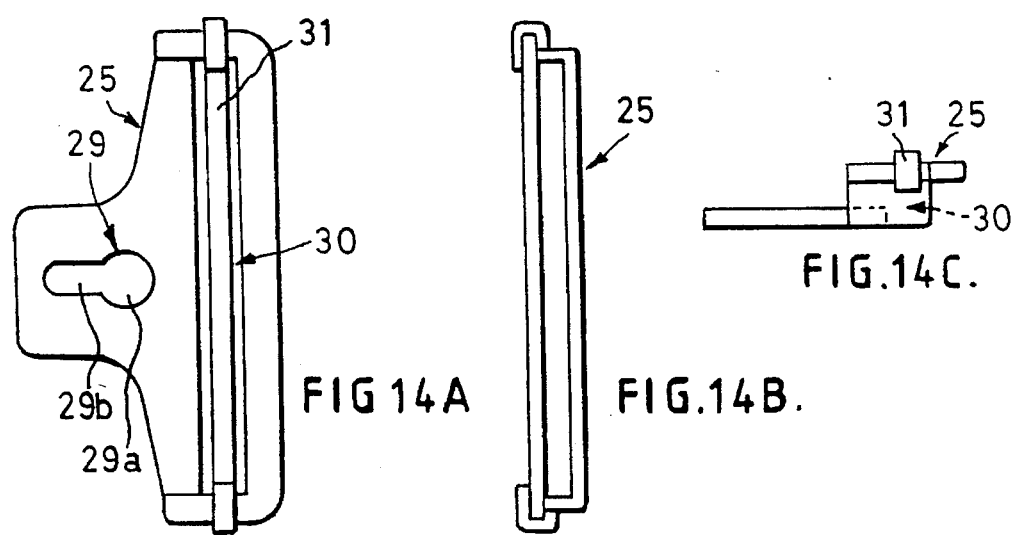
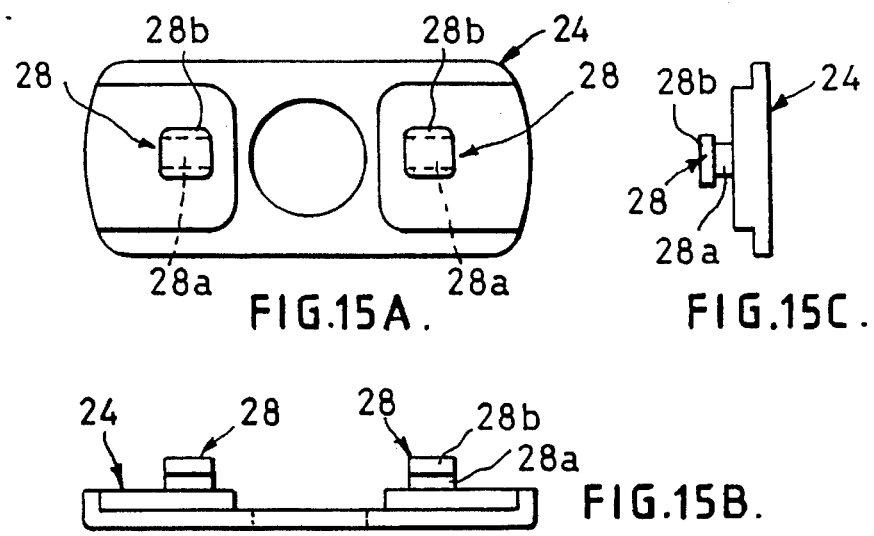

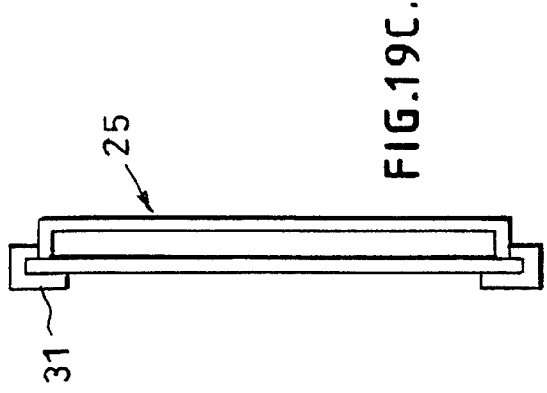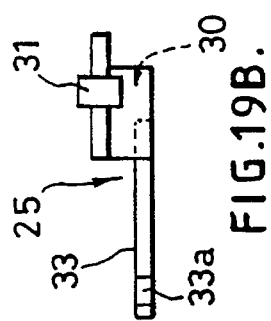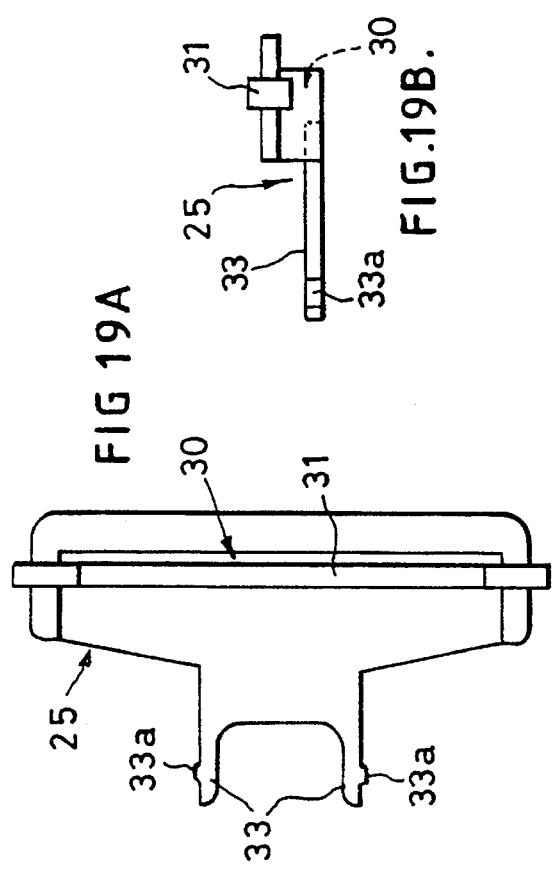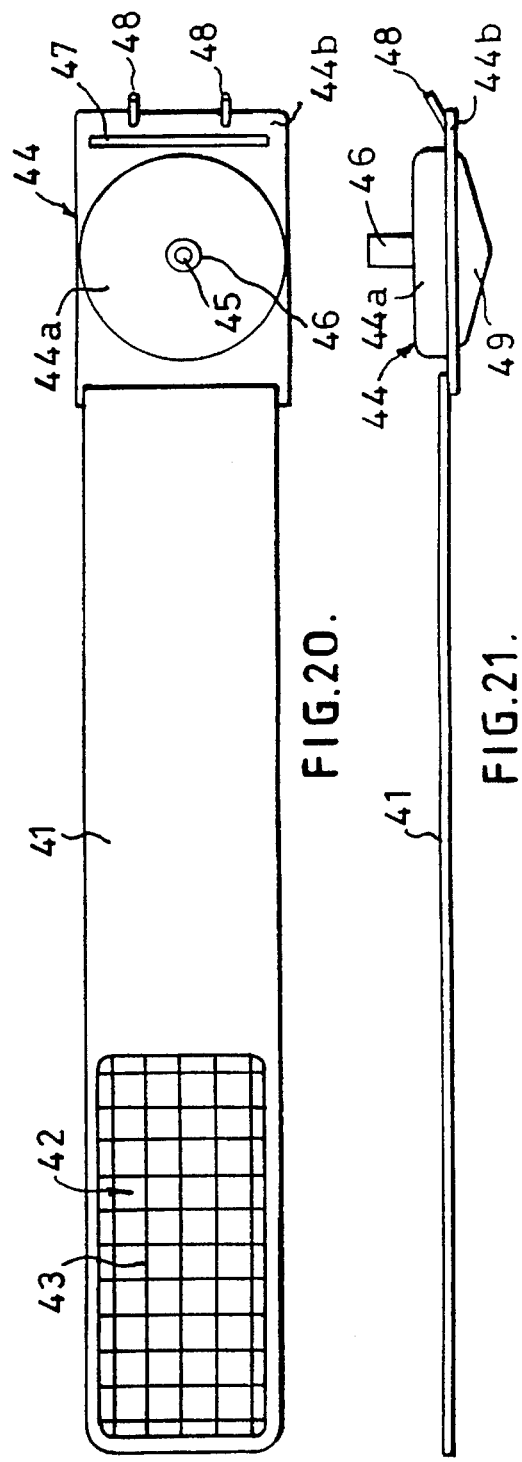

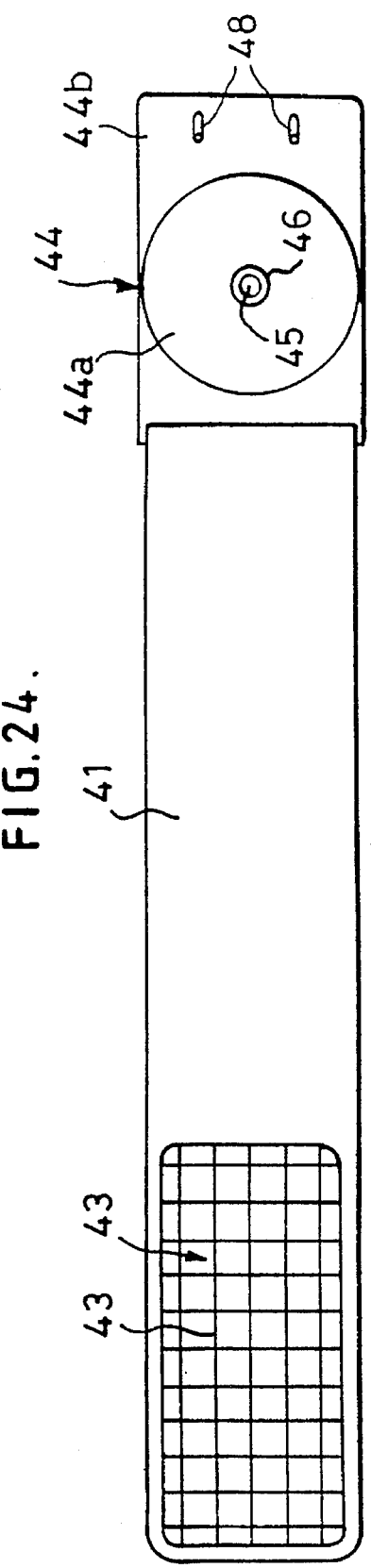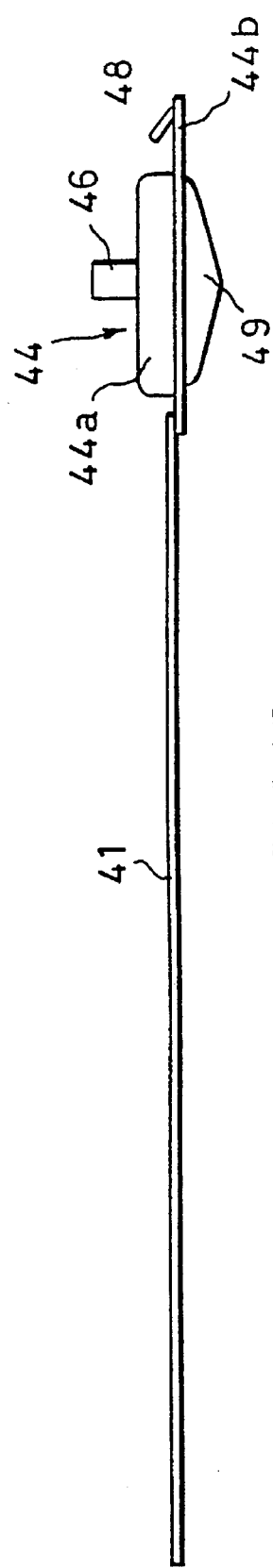

COMPRESSIVE HEMOSTATIC BELT

FIELD OF THE INVENTION

The present invention relates to a compressive hemostatic belt used to stop bleeding from a catheter insertion wound upon completion of an arterial catheter examination.

BACKGROUND OF THE INVENTION

Recently, arterial catheter examinations have been made for contrast medium-using diagnosis of hearts or cerebral blood vessels. Cardiac catheter examinations are made by surgical operation in a few cases but in most cases by the so-called catheter puncture method which moves a catheter from the femoral artery or vein in the inguinal region to the heart. In this examination method, a contrast medium or various medicines are injected through the catheter puncturing the femoral artery or vein in the inguinal region or various preoperative and postoperative examinations are conducted. In this connection, there is a need to compress the catheter insertion wound for a relatively long time in order to stop bleeding from the catheter insertion wound owing to extraction of the catheter from the femoral artery or vein in the inguinal region. Compressive hemostatic methods using adhesive plasters or stretchable belts (see Japanese Patent Application Disclosure Nos. 92746/1985 and 198139/1985) have heretofore been proposed as compressive hemostatic means for such wounds. In the former method, a gauze is applied to the wound and 3 or 4 fabric adhesive plasters are applied to said gauze to compress the wound from above the gauze and a sand bag having a controlled weight of 500–1000 g is placed on said adhesive plasters, said sand bag being fixed in position by adhesive plasters and maintained in this state for 12–24 hours. In this method, however, the sand bag tends to deviate from the region to be compressed, resulting in incomplete hemostasis. Further, the use of adhesive plasters causes such drawbacks to the patient as a stiffening feel, pain and itch and favors the development of skin inflammation and blisters. On the other hand, in the latter method, which uses a stretchable belt, the way of wrapping the belt is complicated and the resulting compressive load is unstable. Further, the use of stretchable belts leads to high cost and they can hardly be thrown away after single use in spite of the fact that reuse involves a hygienic problem of causing hemoinfectious diseases. Therefore, they must be sterilized for prevention of hemoinfectious diseases before they can be reused, imposing limitations not only from a hygienic standpoint but also from the standpoint of enhancing labor saving for nurses.

With the above problems in mind, I have proposed, in Japanese Patent Application No. 20793/1992, a compressive hemostatic belt shown in FIG. 36, as means for stopping bleeding from a wound. This compressive hemostatic belt comprises a pocket 122 in a predetermined position on a band 121 made of non-stretchable or low-stretchable fiber or film, a rigid case 123 and a balloon 124 which are received in said pocket 122. The rigid case 123 is a rigid member made of synthetic resin or the like in bowl form. Further, the balloon 124 is made of rubber or the like and received in the rigid case 123 with a fluid feed tube 126 having a check valve 125 in the pocket 122 and projecting outside. The fluid feed tube 126 for the balloon 124 will have a manual pump 127 and a pressure gauge 128 connected thereto according to the need. Looking at the pressure gauge 128, the operator operates the pump 127, whereby fluid is fed through the fluid feed tube 126 to fill the balloon 124 so that the latter is inflated.

A description of the way of using the compressive hemostatic belt described above will now be given.

As shown in FIG. 37, a gauze B is applied to a catheter insertion wound A and the pocket 122 having the rigid case 123 and balloon 124 received therein is placed on said gauze with the open side of the rigid case 123 directed to the gauze B, whereupon, as shown in FIG. 38, the band 121 is wrapped around the patient's body. That is, the band 121 is wrapped around the leg to cross itself in X-form and the remaining portion is wrapped around the patient's waist one or more turns, the free end being fixed in position by an adhesive plaster. Thereafter, the operator connects the manual pump 127 and pressure gauge 128 to the fluid feed tube 126 of the balloon 126 and, looking at the pressure gauge, operates the pump 127 to fill the balloon 124 with fluid. As shown in phantom lines in FIG. 37, the balloon 129 is inflated against the wound A with the rigid case 123 limiting its inflation to the opposite side, thereby compressing the wound A via the gauze B, the band 121 being firmly fixed to the patient.

Since the above compressive hemostatic belt compresses the wound A by utilizing the inflation of the balloon 124 in the manner described above, it is possible to compress the wound A alone with no compressive feeling transmitted to the other parts of the patient's body. Operating the pump 127 while looking at the pressure gauge 128 allows the selection of the desired size of the compressive force to be applied to the wound A. The selected compressive force being applied to the wound A can be maintained for a long time by the check valve 125. Since a non-stretchable or low-stretchable fabric is used for the band 121, the occurrence of a stiffening feel, pain or itch can be avoided and so can skin inflammation and blisters. Further, the belt can be presented at low cost and thrown away after single use. Other remarkable effects are also developed in respect of improvements in hygiene and enhanced labor saving.

Since the conventional compressive hemostatic belt has its band 121 made in straight form, the fitness of the belt as wrapped in X form around the leg is poor, producing positional deviation or slack during a lone period of compressive hemostasis, resulting in unsatisfactory compression of the wound. The portions of the belt wrapped around the patient's leg and waist tend to form wrinkles, thus developing an uncomfortable feeling in the patient and positional deviation or slack is produced by wrinkles or twist, making it difficult to provide a stabilized compressive force. Further, the end of the band 121 is locked by locking means, such as a double-coated tape or magic tape. Such double-coated tapes or magic tapes tend to decrease their adhesive power during repeated use. There is a danger of the band slacking or coming off during wearing. Since the position where the locking means is fastened differs from patient's figure to figure, several bands different in length have to be prepared according to patients' figures.

I have proposed, in Japanese Patent Application No. 153155/1993, a compressive hemostatic belt which remedies the drawbacks described above. This belt includes a rotatable buckle having slits in the opposite sides and integral with the band and the rigid case having the balloon received therein. Band holding jigs are installed on the opposite sides of the buckle. Each jig comprises a fixed portion extending integrally from the buckle and a movable portion rotatably supported on the fixed portion. The movable portion has a cross section which is asymmetrical with respect to its axis of rotation and the clearance between the movable and fixed portions is increased when the band is passed, said clearance disappearing when the band is fixed in position. According to this compressive hemostatic belt, since the ends of the band are locked by utilizing the band holding jigs, effective compressive hemostasis is achieved without the danger of the band coming off or slacking during wearing. Further, any desired portions of the band can be locked by the jigs; therefore, if the remaining excessive portion, if any, of the band is cut off by scissors, a single type of band which is a little longer in size can be applied to almost all patients.

However, when the ends of the band of said compressive hemostatic belt are to be locked, the ends of the band have to be passed through the slits of the buckle and turned back to pass between the movable and fixed portions of the band holding jigs. Since the buckle and band holding jigs are integrally attached to the rigid case, said operation is hard to perform, retarding the wrapping operation or leading to troubles.

Another problem is that since the band 121 which is made of non-stretchable or low-stretchable fiber, nonwoven fabric or film is wrapped around the body, which is undulating or wavy, the band 121 tends to float off the skin when the leg is raised, leading to poor fitness. As a result, when the compressive hemostasis continues for a long time, the band wrinkles or twists to arouse an uncomfortable feeling in the patient and such wrinkles or twist causes positional deviation or slack, thus making the compression of the wound insufficient.

In the compressive hemostatic belt described above, a check valve is attached to the outer end of the fluid feed tube 126 in order to hold the fluid in the balloon 124 for a long time. Since this check valve 125 should have a holding power of more than 24 hours, it is made in precision construction in consideration of reliability, leading to a high cost. Thus, the cost of the check valve 125 is high and if this compressive hemostatic belt is thrown away after single use, it becomes expensive and is disadvantageous from an economic point of view.

The check valve 125 has to be constructed to allow fluid to flow in and out. However, the check valve 125 constructed to allow fluid to flow in and out is complicated in construction and expensive, leading to an increase in the cost of the compressive hemostatic belt and making it uneconomical to throw away the belt after single use. Further, the check valve constructed to allow fluid to flow in and out does not allow fluid to flow out in the state in which the connecting hose of the fluid flow in-and-out pump 127 is connected. Thus, when the fluid is pumped into the balloon 124 by the fluid flow in-and-out pump 127, the compressive force can be ascertained by the pressure gauge 128, but it cannot be ascertained when the fluid flows out of the balloon 124. Thus, adjustment of the compressive force has been very inconvenient.

An object of the present invention is to provide a compressive hemostatic belt having improved fitness on the body, prevented from wrinkling or twisting, and designed so that the band can be easily wrapped and the ends of the band can be easily locked.

Another object of the invention is to provide a compressive hemostatic belt prevented from coming off or slacking after being wrapped and wherein a single type is sufficient for all band lengths.

Another object of the invention is to provide a compressive hemostatic belt which is sufficiently inexpensive to be advantageously thrown away after single use.

A further object of the invention is to provide a compressive hemostatic belt designed for convenient adjustment of compressive force and a fluid flow in-and-out pump for use with it.

SUMMARY OF THE INVENTION

To achieve the above objects, the invention provides a compressive hemostatic belt wherein a balloon adapted to be inflated by being filled with fluid is attached to a predetermined position on a band made of non-stretchable or low-stretchable fiber, nonwoven fabric or film by any desired attaching means, said compressive hemostatic belt being characterized in that at least that portion of said band which corresponds to the leg when the band is wrapped around the body is shaped in curve form. The portions of the band corresponding to the leg and waist when the band is wrapped around the body have cores embedded therein. The portions of the band corresponding to the leg and waist when the band is wrapped around the body are formed of reinforcing members. A buckle having slits in the opposite ends is rotatably attached to the band and locking means which can be removed by a single manipulation are installed on the opposite sides of the band. Said buckle is integrally attached together with the band through a member having a through-hole to a rigid case having said buckle received therein. Shaping in curve form at least the portion of the band corresponding to the leg when the band is wrapped around the body provides improved fitness on the leg, preventing positional deviation or slack even if the compressive hemostasis continues for a long time. Embedding cores in the portions of the band corresponding to the leg and waist when the band is wrapped around the body and forming said portions from a reinforcing member prevents said portions from wrinkling or twisting. Rotatably attaching a buckle having slits in the opposite ends to the band and installing locking means which can be removed by a single manipulation on the opposite ends of the band makes it easier to wrap the band around the body and to handle, by locking, the end of the portion of the band remaining after wrapping. Integrally attaching the buckle together with the band through a member having a through-hole to the rigid case having the balloon received therein provides easy ascertainment of the inflated state of the balloon.

According to the invention, buckles are attached to the opposite ends of the band and a buckle attaching plate for removably mounting said buckles is rotatably attached to said rigid case.

Thereby, the opposite ends of the band can be locked by simply mounting the buckles on said buckle attaching plate during wrapping. According to the invention, one or more projections are formed on one end portion of the band or said rigid case so that the other end portion of the band can be thrusted on said projections. The front ends of said projections can be needle-shaped. The intermediate portions of said projections can be decreased in strength to allow the front ends to be broken. The front ends of said projections can be shaped in approximately semicircular form and the end of the band can be formed with one or more holes for said projections to extend therethrough. A buckle having a slit for the band to extend there through and projections for the end of the band to be thrusted thereon can be attached to said one end portion of the band or said rigid case.

Forming one or more projections on one end portion of the band or said rigid case for the other end portion of the band to be thrusted on said projections enables the band to be fixed in position at any desired place on the band by thrusting the other end portion of the band on the projections after wrapping of the band, while the remaining portion of the band can be dealt with by cutting it off as by scissors. Shaping the front ends of the projections in needle form enables the band to be fixed in position by thrusting the other end portion of the band on the projections after wrapping of the band. Decreasing the strength of the intermediate portions of the projections to allow the front ends to be broken off enables the front ends of the projections to be removed by breaking them off after the other end portion of the band has been thrusted on the projections. Shaping the front ends of the projections in approximately semicircular form and forming the end of the band with one or more holes to be inserted on the projections enables the band to be fixed in position by inserting the holes on the projections after wrapping of the band. Attaching a buckle having a slit for the band to extend therethrough and projections for the end of the band to be thrusted thereon to said one end portion of the band or said rigid case enables the band to be fixed in position by pulling the band in the direction of reaction when the other end portion of the band is inserted in the slit after the wrapping of the band.

According to the invention, the whole or part of said band is made of adhesive material. The band is made of a material having non-stretchability or low-stretchability. More concretely, it is made of nonwoven fabric, paper, film or the like.

Since the whole or part of the band is made of adhesive material, it can be fixed by being stuck to the patient's body. Since the band is made of non-stretchable or low-stretchable textile fabric, nonwoven fabric, film or the like, it can be presented at low cost and easily put into practical use as it can be advantageously thrown away after single use.

According to the invention, a check valve is removably mounted on the balloon.

The compressive section is composed of a balloon, a fluid feed tube for filling said balloon with fluid, and a check valve removably mounted on said fluid feed tube, said check valve being removably mounted by being fitted or screwed on the end of the fluid feed tube, with a seal member such as a packing interposed between the check valve and the fluid feed tube.

Since a check valve is removably mounted on the balloon, the check valve, which is expensive, can be removed for reuse. As described above, the compressive section is composed of a balloon, a fluid feed tube for filling said balloon with fluid, and a check valve removably mounted on said fluid feed tube, said check valve being removably mounted by being fitted or screwed on the end of the fluid feed tube, with a seal material such as a packing interposed between the check valve and the fluid feed tube. As a result of this arrangement, mounting and dismounting of the check valve is easy and the seal material prevents fluid from leaking between the check valve and the fluid feed tube.

The present invention provides a compressive hemostatic belt using a check valve sealed by internal pressure, and also provides a fluid flow in-and-out pump connected to the check valve of said compressive hemostatic belt and having a presser pin in the front end of a connecting hose for opening said check valve.

When the connecting hose of the fluid flow in-and-out pump is connected to the check valve of the compressive hemostatic belt, the presser pin opens the check valve to allow fluid to flow in and out, and the pressure can be ascertained even when the fluid is allowed to flow out, a fact which is convenient for adjusting the compressive force.

BRIEF DESCRIPTION OF THE DRAWINGS

FIG. 1 is a plan view of a compressive hemostatic belt according to a first embodiment of the invention;

FIG. 2 is an enlarged view of the buckle portion of said belt;

FIG. 3 is a plan view of said buckle;

FIG. 4 is a side view of said buckle;

FIGS. 5A through 5C are perspective views for explaining how to tighten the compressive hemostatic belt;

FIG. 6 is a plan view of a compressive hemostatic belt according to a second embodiment of the invention;

FIG. 7 is an enlarged view showing a buckle attaching plate of the belt;

FIG. 8 is a front view of a balloon;

FIG. 9 is a sectional view of said balloon;

FIG. 10A is a plan view of the buckle attaching plate;

FIG. 10B is a front view of said plate;

FIG. 10C is a side view of said plate;

FIGS. 11A and 11B are perspective views for explaining how to tighten the compressive hemostatic belt;

FIG. 12 is an enlarged plan view of the end of the compressive hemostatic belt showing the joining of the buckle;

FIG. 13 is a sectional view of said view;

FIG. 14A is a plan view of the buckle attaching plate;

FIG. 14B is a front view of the buckle attaching plate;

FIG. 14C is a side view of the buckle attaching plate;

FIG. 15A is a plan view of a buckle attaching plate having an engaging member of different shape;

FIG. 15B is a front view of said attaching plate;

FIG. 15C is a side view of said attaching plate;

FIG. 19A is a plan view of a buckle used in said different embodiment;

FIG. 19B is a front view of said buckle;

FIG. 19C is a side view of said buckle;

FIG. 20 is a plan view of a compressive hemostatic belt according to a third embodiment of the invention;

FIG. 21 is a side view of said belt;

FIG. 24 is a plan view of a compressive hemostatic belt according to another embodiment;

FIG. 25 is a side view of said belt;

Description of Preferred Embodiments

An embodiment of the invention will now be described with reference to FIGS. 1 through 5C.

DESCRIPTION OF THE PREFERRED EMBODIMENTS

Figure 36:
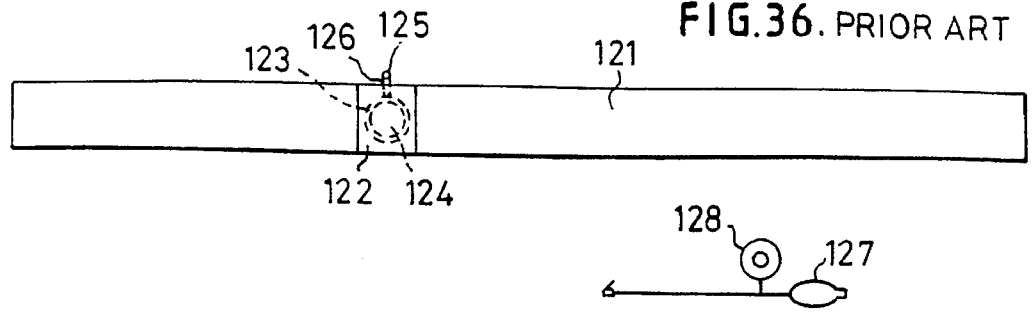
FIG. 36 is a plan view of a conventional compressive hemostatic belt.
Figure 37:
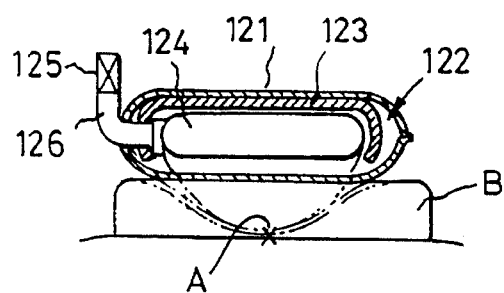
FIG. 37 is a side view of a balloon mounted on an affected part.
Figure 38:
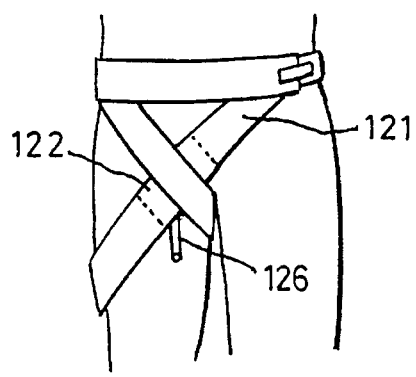
FIG. 38 is a perspective view of the compressive hemostatic belt mounted on an affected part.
Figure 39:
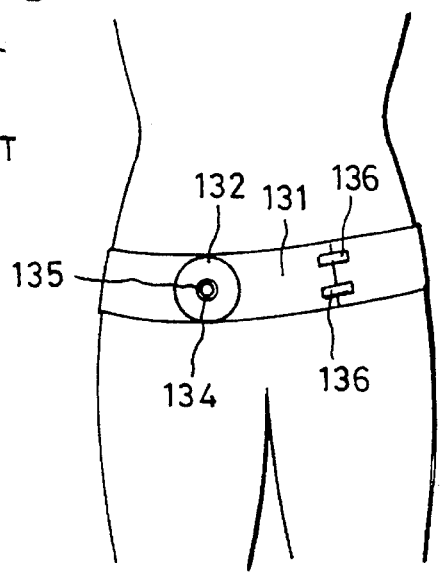
FIG. 39 is a perspective view of the compressive hemostatic belt mounted on an affected part, showing a different state of mounting.
Figure 40:
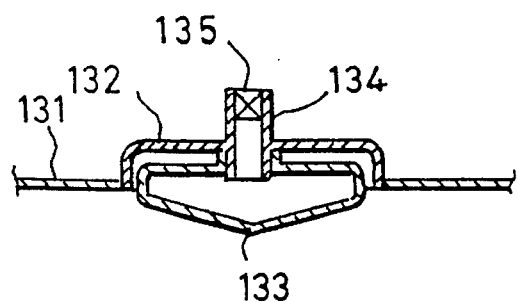
FIG. 40 is a sectional view of a balloon.
Figure 41:
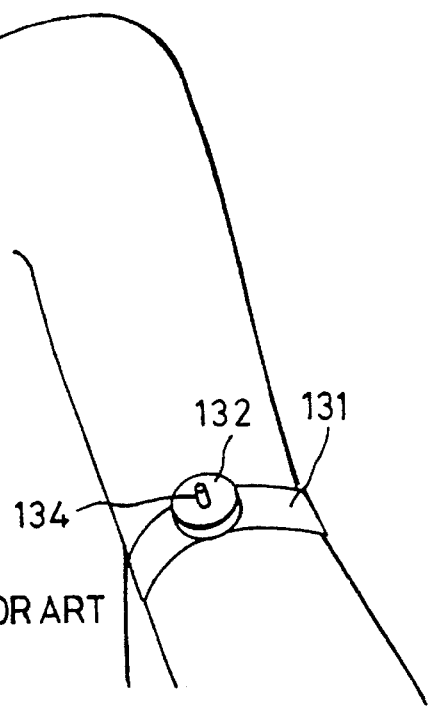
FIG. 41 is a perspective view of the compressive hemostatic belt mounted on an affected part, showing a different state of mounting.
Figure 42A:
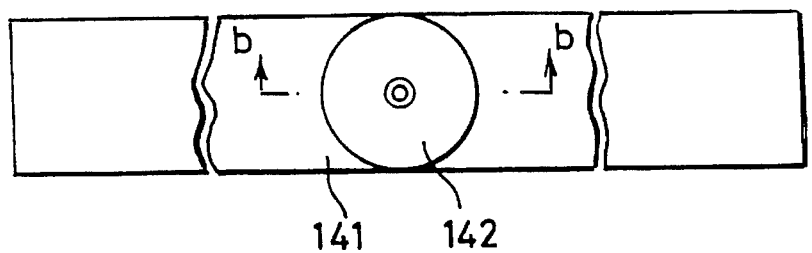
FIG. 42A is a plan view of a compressive hemostatic belt.
Figure 42B:
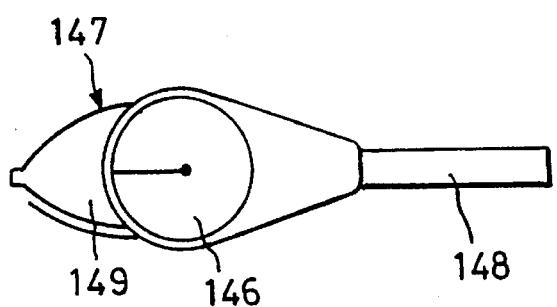
FIG. 42B is a plan view of a pump.

FIG. 1 is a plan view of a compressive hemostatic belt according to the present invention. This compressive hemostatic belt, like a conventional article shown in FIG. 36, has a band 1 made of non-stretchable or low-stretchable fiber, nonwoven fabric or film. The band 1 is formed with a pocket 2 at a predetermined position, said pocket 2 having received therein a rigid case and a balloon.

The rigid case is made of synthetic resin or the like in bowl form. The balloon is made of rubber or the like and received in the rigid case with its fluid feed tube 6 projecting outside the pocket 2, said fluid feed tube 6 having a check valve 5.

In the present invention, at least that portion of the band 1 which is wrapped around the human leg during wrapping around the human body, or a leg wrapping portion 1a, is shaped in curve form. That is, the longitudinal axis of a portion of the band 1 lying in the plane of the band is curved away from an extension of the longitudinal axis of the remainder of the band. This leg wrapping portion 1a and a waist wrapping portion 1b to be wrapped around the waist have embedded therein cores 9 and 10 made of PET or thick paper. The core 9 inserted in the leg wrapping portion 1a is depressed to avoid contact with the crotch. Thereby, the leg wrapping portion 1a of the band 1 can be wrapped around the leg with ease and good fitness by utilizing the curved form. The band 1 can be reliably wrapped around the human body with the cores 9 and 10 preventing the leg wrapping portion 1a and waist wrapping portion 1b from forming wrinkles. Thus, the improved fitness on the leg prevents positional deviation or slack even if compressive hemostasis continues for a long time, thereby ensuring effective compressive hemostasis. Prevention of wrinkles or twist precludes the possibility of an uncomfortable feeling being aroused in the patient, and positional deviation or slack due to wrinkles or twist is also eliminated.

In the present invention, a buckle attaching plate 11 having slits 11a and 11b in the opposite ends, as shown in FIGS. 3 and 4, is rotatably attached through a center pin 12 having a through-hole 12a so that it is integral with the band 1 and the rigid case received in the pocket 2 of said band 1. Locking members 13 which can be engaged and disengaged by a single manipulation, such as double-coated tapes, magic tapes or buttons, are disposed on the opposite ends of the band 1. Thereby, the band 1 can be easily wrapped around the body by utilizing the rotatable buckle attaching plate 11. The opposite ends of the portion of the band 1 remaining after wrapping can be easily locked by utilizing the locking members 13. It has become possible to ascertain the inflation of the balloon through the through-hole 12a in the center pin 12. Therefore, by wrapping the band 1 around the body by utilizing the rotatable buckle plate 11, the float caused by the difference in angle at the time of wrapping owing to the difference in the figure of the body can be eliminated and so can the positional deviation. Since the opposite ends of the portion of the band remaining after wrapping are locked by utilizing the locking members 13 which can be engaged or disengaged by a single manipulation and which are attached to these ends, the time to prepare adhesive plasters for locking the ends of the band is eliminated; thus, the ends of the band can be smoothly locked. The presence of the through-hole 12a in the middle of the center pin 12 enables the inflation of the balloon to be easily ascertained by sight, by the feel or by a gauge.

How the compressive hemostatic belt according to the present invention is wrapped around the body will now be described.

First, as shown in FIG. 5A, the leg wrapping portion 1a of the band 1 is wrapped around the leg and then the waist wrapping portion 1b of the band 1 is wrapped around the waist from the back to the front, whereupon, as shown in FIG. 5B, the opposite ends of the band 1 are passed through the slits 11a of the buckle plate 11 and then, as shown in FIG. 5C, the opposite ends of the band 1 are locked to the ends of the leg and waist wrapping portions 1a and 1b by the locking members 13.

In the above embodiment, as means for preventing wrinkles or twist from being produced in the portions 1a and 1b corresponding to the leg and waist as the band 1 is wrapped around the body, the cores 9 and 10 have been inserted therein. Alternatively, the portions 1a and 1b may be formed of a reinforcing member made of resin-coated or resin-impregnated fiber or nonwoven fabric.

In the above embodiment, the opposite ends of the band 1 are locked by the locking members 13 which can be engaged or disengaged by a single manipulation, such as double-coated tapes, magic tapes or buttons. Alternatively, the slits 11a of the buckle plate 11 may be made closable to grip the ends of the band 1 or may be formed with projections adapted to be inserted in holes formed in the band 1 to thereby lock said ends.

In the above embodiment, the rigid case and balloon have been received in the pocket 2 formed in the band 1. However, since the buckle plate 11 is made integral with the band 1 and rigid case by the center pin 12, the pocket 2 may be dispensed with.

As has been described so far, according to the present invention, fitness on the leg is improved to prevent positional deviation and slack even if compressive hemostasis continues for a long time, thus ensuring efficient compressive hemostasis. The leg and waist portions of the band can be prevented from wrinkling or twisting, thereby eliminating the possibility of arousing an uncomfortable feeling in the patient, and the positional deviation and slack due to wrinkles or twist are also eliminated. The wrapping of the band is facilitated by the buckle, and the ends of the portion remaining after wrapping can be easily dealt with by locking them, thereby providing improved labor saving for nurses and improved wrapped conditions fit to the patient's figure. Since the inflation of the balloon can be ascertained, hyperemia and hematoma due to excessive compression can be avoided.

A second embodiment of the present invention will now be described with reference to FIGS. 6 through 19C.

FIG. 6 is a plan view of a compressive hemostatic belt according to a second embodiment of the invention; FIG. 7 is a fragmentary enlarged plan view of said compressive hemostatic belt; FIG. 8 is a fragmentary enlarged bottom view of said compressive hemostatic belt; and FIG. 9 is a fragmentary enlarged longitudinal sectional view of said compressive hemostatic belt.

As shown in FIGS. 6 through 9, the compressive hemostatic belt according to the present invention has a rigid case 22 suitably attached to a predetermined position on a band 21 made of non-stretchable or low-stretchable fiber, non-woven fabric or film. A balloon 23 capable of being inflated by being filled with fluid is received in said rigid case 22. A buckle attaching plate 24 is rotatably attached to the rigid case 22, and buckles 25 mountable on said buckle attaching plate 24 are attached to the opposite ends of the band 21.

The rigid case 22 is made of a rigid material, such as synthetic resin, in bowl form. Its upper surface is integrally centrally formed with an attaching boss 22a extending through the band 21. The buckle attaching plate 24 is rotatably attached to the front end of the attaching boss 22a projecting beyond the band 21.

The balloon 23 is made of an elastic material, such as rubber, in bag form and received in the rigid case 22 with a fluid feed tube 27 projecting outward, said fluid feed tube 27 having a check valve 26. A manual pump and a pressure gauge will be connected to the fluid feed tube 27 of the balloon 23 according to the need. While looking at the pressure gauge, the operator operates the pump to fill the balloon 23 with fluid so as to inflate the latter.

The buckle attaching plate 24 is rotatably attached to the attaching boss 22a of the rigid case 22. As shown in FIGS. 10A through 10C, engaging members 28 are installed on the upper surface of the plate 24. Each engaging member 28 comprises a shaft portion 28a projecting integrally from the upper surface of the buckle attaching plate 24 and a head portion 28b of large diameter formed on said shaft portion, with an engaging clearance defined between the upper surface of the buckle attaching plate 24 and the head portion 28b and being approximately equal to the thickness of the buckle 25.

The buckle 25, as shown in FIGS. 11A and 11B, is formed at the front end of its narrow portion with an engaging hole 29 for engagement with the engaging member 28 of the buckle attaching plate 24. The rear portion of the buckle 25 is formed with a slit 30 for the band 21 to be inserted therein for fixing. The engaging hole 29 comprises a circular through-hole portion 29a and a U-shaped grip portion 29b communicating therewith. The through-hole portion 29a has a diameter slightly greater than that of the head portion 28b of the engaging member 28. The grip portion 29b has a sufficient size for the shaft portion 28a of the engaging member 28 to fit therein. After the head portion 28a of the engaging member 28 has been passed through the through-hole portion 28a, the grip portion 29b is thrusted on the shaft portion 28a of the engaging member 28 to fit the buckle 25 between the upper surface of the buckle attaching plate 24 and the head portion 28b. Thus, as shown in FIGS. 12 and 13, the buckle 25 can be mounted on the buckle attaching plate 24 by a single manipulation. The slit 30 has a slide member 31 slidably mounted thereon, so that as shown in FIGS. 12 and 13 the end of the band 21 is inserted in the slide member 31 to extend therearound and then the slide member 31 is slid, thereby attaching the buckle 25 to the end of the band 21.

The wrapping of the compressive hemostatic belt according to the present invention will now be described; the case of wrapping it around the leg will be taken as an example.

First, as shown in FIG. 11A, while the rigid case having the balloon 23 received therein is placed on the catheter insertion wound, the band 21 is wrapped around the leg. Subsequently, one end portion of the band 21 is wrapped around the waist from the back to the front and then as shown in FIG. 11B, the buckles 25 attached to the ends of the band 21 in advance are mounted on the buckle attaching plate 24 by utilizing the engaging holes 29 and the engaging members 28. Finally, the opposite ends of the band are pulled to adjust the tightening force to complete the wrapping. Thereafter, the operator connects the manual pump and pressure gauge to the fluid feed tube 27 of the balloon 23 and while looking at the pressure gauge he operates the manual pump to fill the balloon 23 with fluid. The balloon 23 is inflated toward the catheter insertion wound to compress the latter while it is restricted by the rigid case 22 from inflating toward the opposite side.

According to the compressive hemostatic belt of the present invention, if the buckles 25 are attached to the ends of the band 21 in advance, the opposite ends of the band 21 can be fixed in position simply by mounting the buckles 25 on the buckle attaching plate by a single manipulation. Since the buckles 25 are separate from the rigid case 22, the insertion of the ends of the band 21 into the buckles 25 is easier. Further, since the buckle attaching plate 24 is rotatable with respect to the rigid case and since the buckles 25 are rotatable with respect to the buckle attaching plate 24, the band can be wrapped with good fitness around the body of a patient having any figure and positional displacement or slack will not be produced even if compressive hemostasis continues for a long time. Thus, effective compressive hemostasis can be achieved.

The invention is not limited to the above embodiment. For example, as shown in FIGS. 10 and 11, the engaging members 28 of the buckle attaching plate 24 and the engaging holes 29 of the buckles 25 may be made rectangular. In this case, basically the buckles 25 are not rotatable with respect to the buckle attaching plate 24; however, by suitably designing the shape of the shaft portion 28a of the engaging member 28, the buckles 25 can be made rotatable with respect to the buckle attaching plate 24 in a predetermined angle range.

Figure 16A:
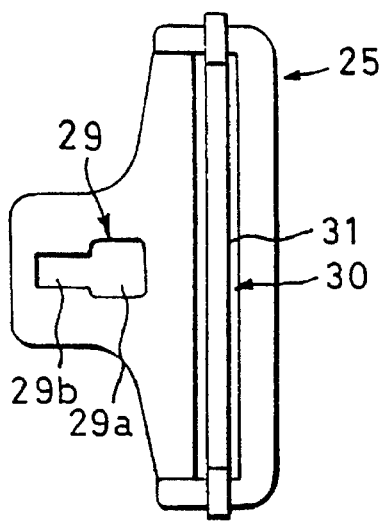
FIG. 16A is a plan view of a buckle having an engaging hole of different shape.
Figure 16C:
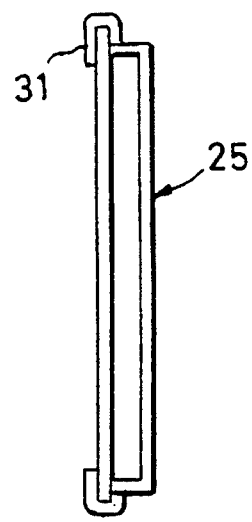
FIG. 16C is a side view of said buckle.
Figure 16B:
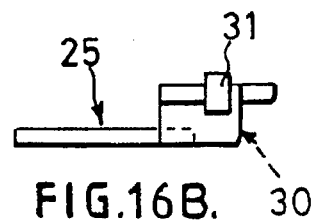
FIG. 16B is a front view of said buckle.
Figure 17:
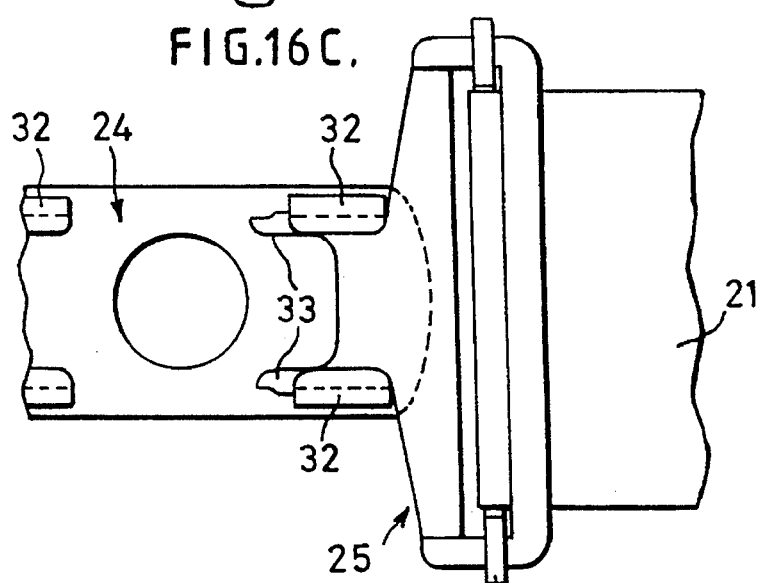
FIG. 17 is a plan view of a buckle and a buckle attaching plate which are joined together in a different embodiment.
Figure 18A:
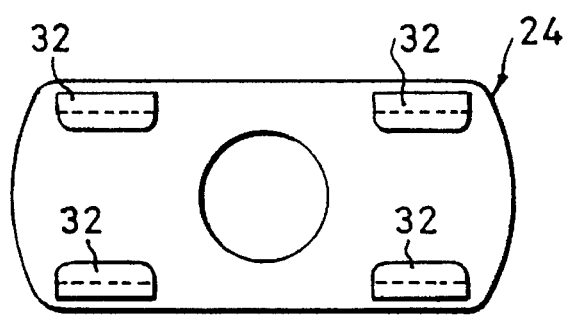
FIG. 18A is a plan view of a buckle attaching plate used in said different embodiment.
Figure 18C:
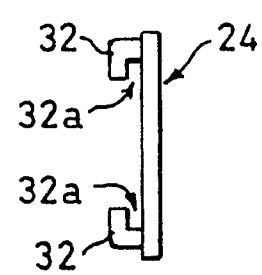
FIG. 18C is a side view of said attaching plate.
Figure 18B:
FIG. 18B is a front view of said attaching plate.

Further, in the above embodiment, it is arranged that the buckles 25 can be mounted by a single manipulation on the buckle attaching plate 24 by utilizing engagement between the engaging members 28 of the buckle attaching plate 24 and the engaging holes 29 of the buckles 25; however, as shown in FIG. 17, the buckles 24 can be mounted on the buckle attaching plate 24. That is, as shown in FIGS. 18A through 18C, pairs of grooved frames 32 of inverted L-shaped cross section each having an insertion groove 32a are disposed on the upper surface of the buckle attaching plate 24, the grooved frames in each pair being spaced a predetermined distance. As shown in FIGS. 19A through 19C, the narrow front end of each buckle 25 is bifurcated to form a pair of elastic engaging elements 33 having engaging pawls 33a. The buckles 25 can be mounted by a single manipulation on the buckle attaching plate 24 by inserting the elastic engaging elements 33 of the buckles 25 into the insertion grooves 32a of the grooved frames 32 of the buckle attaching plate 24 to engage the engaging pawls 33a of the elastic engaging elements 33 with the end edges of the grooved frames 32.

The compressive hemostatic belt of the present invention is not limited in use to blood vessel catheter examinations but is also applicable to stoppage of bleeding from a wound caused by a catheter treatment, kidney or other dialysis, or an injection using various needles.

As has been described so far, according to the present invention, if the buckles are attached to the ends of the band in advance, the opposite ends of the band can be fixed in position simply by mounting the buckles on the buckle attaching plate by a single manipulation, so that the wrapping of the band around the body can be smoothly effected. Since the insertion of the ends of the band into the buckles is easy, the operating efficiency is greatly increased.

A third embodiment of the invention will now be described with reference to FIGS. 20 through 28.

In FIGS. 20 and 21, the numeral 41 denotes a band made of non-stretchable or low-stretchable fiber, nonwoven fabric or film. The band 41 is formed with a window opening 42 having a mesh element 43 stretched thereon. The mesh element 43 may be made of any desired material. For example, a grid mesh structure punched out of a plastic sheet may be used. The numeral 44 denotes a buckle-like rigid case attached to one end of the band 41 by any suitable means and comprising a rigid case portion 44a made of synthetic resin in bowl form, and a buckle portion 44b integrally formed on the open side of said rigid case portion 44a. The upper surface of the rigid case portion 44a is integrally formed at the center with a fluid feed tube 46 having a check valve 45 at its outer end. The buckle portion 44b has a slit 47 through which the band 41 is passed. The buckle portion 44b is formed with a pair of projections having approximately semicircular front ends adapted to thrust through the mesh element 43. The numeral 49 denotes a balloon received in the rigid case 44 and adapted to be inflated by being filled with fluid, said balloon being made of a stretchable material, such as rubber. The opening in said balloon 49 is fixed by any suitable means to the inner end of the fluid feed tube 46 extending into the rigid case portion 44a.

How to wrap the compressive hemostatic belt according to the invention will now be described.

Figure 22:
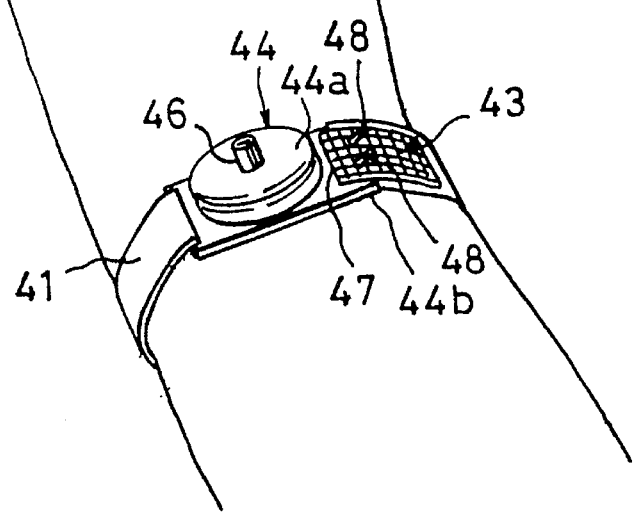
FIG. 22 is a perspective view showing how to wrap said belt around the human body.
Figure 23:
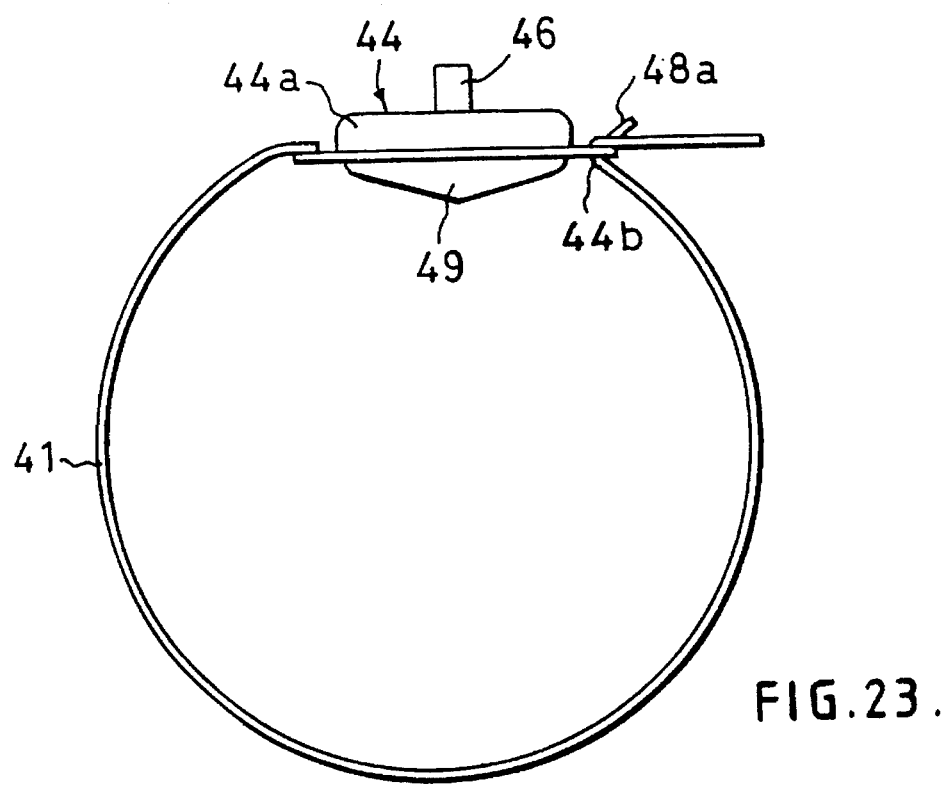
FIG. 23 is a side view of the belt in the wrapped state.

As shown in FIGS. 22 and 23, the buckle-like rigid case 44 having the balloon 49 received therein is placed on a gauze applied to a catheter insertion wound with the open side of the rigid case being directed to the gauze. Thereafter, the band 41 is wrapped around the wounded part and the end of the band is led to the buckle portion 44b of the rigid case 44 and is passed through the slit formed in the buckle portion 44b and is turned back. The mesh element 43 stretched on the end of the band 41 is thrusted on the projections 48 formed on the buckle portion 44b of the rigid case 44 and the band 41 is pulled in the direction of reaction and fixed at a desired place thereon. The excessive portion of the band 41 remaining after wrapping is cut off as by scissors. Thereafter, the manual pump and pressure gauge are connected to the fluid feed tube 46. Looking at the pressure gauge, the operator operates the pump to fill the balloon 49 with fluid. The balloon 23 is inflated toward the catheter insertion wound to compress the latter while it is restricted by the rigid case portion 44a of the buckle-like rigid case 44 from inflating toward the opposite side.

According to the compressive hemostatic belt of the present invention, after the wrapping of the band 41, the band 41 is fixed in position by thrusting the mesh element 43 stretched on the end of the band 41 on the projections 48 set in the buckle portion 44b and pulling the band 41. The wrapping stability of the band 41 is improved without the possibility of the band 41 being slacked by the reverse movement of the band. Therefore, effective compressive hemostasis can be achieved without the possibility of the band 41 coming off or slacking. Further, since the band 41 can be fixed at any desired place thereon, if the excessive portion of the band 41 remaining after wrapping is disposed of by being cut off as by scissors, then a single kind of band which is a little longer can be applied to almost all patients. The need for preparing a number of bands 41 different in length as in the prior art has been eliminated.

Figure 26:
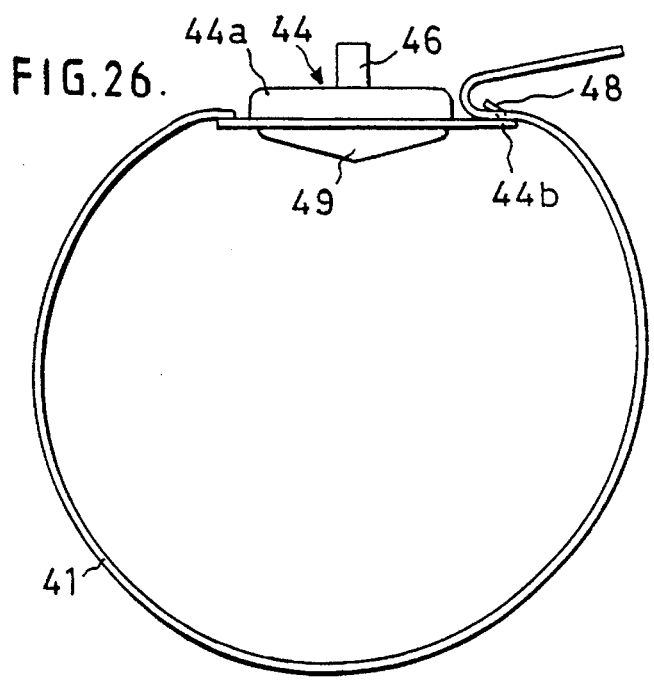
FIG. 26 is a side view of the belt in the wrapped state.

In addition, the present invention is not limited to the above embodiment. As shown in FIGS. 24 and 25, the buckle portion 44b of the rigid case 44 may be provided with projections 48 which are slanted toward the middle of the rigid case 44, so that the band is wrapped around the wounded part caused by catheter insertion and its end is led to the buckle portion 44b, whereupon, as shown in FIG. 26, the mesh element 43 stretched on the end of the band 41 is thrusted on the projections 48 to thereby fix the band 41 in position.

Figure 27:
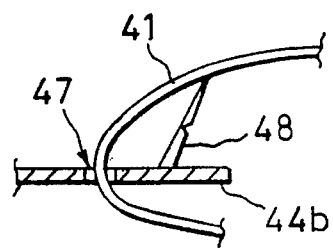
FIG. 27 is a side view of a needle-like projection prior to thrusting through the belt.

Further, as shown in FIG. 27, a number of holes may be formed in the end of the band 41, so that said holes are inserted on the projections 48 set in the buckle portion 44b of the rigid case 44 to thereby fix the band 41 in position.

Figure 28:
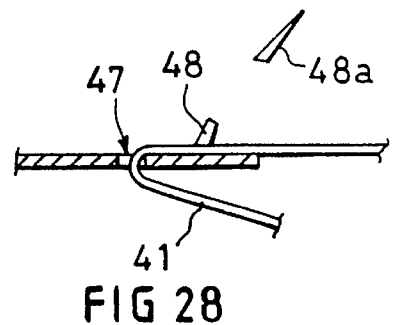
FIG. 28 is a side view of said needle-like projection after thrusting through the belt.

Further, as shown in FIG. 27, the front ends of the projections 48 may be shaped in needle form so that the band 41 can be thrusted on the projections 48 to be thereby fixed in position. In this case, if the strength of the projections is locally decreased as by forming a cut in the intermediate portion of each projection, the front end portions 48a of the projections 48 can be broken off as shown in FIG. 28, thus eliminating the danger of scratching the skin.

The compressive hemostatic belt of the present invention is not limited in use to blood vessel catheter examinations but is also applicable to stoppage of bleeding from a wound caused by a catheter treatment, kidney or other dialysis, or an injection using various needles.

As has been described so far, according to the present invention, the band can be fixed at any desired place thereon by thrusting the end of the band on the projections after wrapping of the band; therefore, there is no possibility of the slacking of the band by the reverse movement. The wrapping stability of the band is improved without the possibility of the band coming off or slacking, thus ensuring effective compressive hemostasis. The locking means, such as double-coated tapes and magic tapes, provided on the opposite ends of the band as in the prior art is no longer necessary, making it possible to decrease the production cost. If the excessive portion of the band remaining after wrapping is disposed of by cutting off as by scissors, a single kind of band which is a little longer can be applied to almost all patients. When hemostasis has been attained to some extent, it is desirable to weaken the compressive force so as to reduce the burden on the patient. In the compressive hemostatic belt according to the present invention, this can be attained simply by displacing the position of the band at which it is locked by the projections to adjust the compressive force.

A fourth embodiment of the invention will now be described with reference to FIG. 29.

In this compressive hemostatic belt, the band 61 is made entirely of an adhesive material, such as a fabric adhesive plaster. A rigid case 63 for receiving a balloon adapted to be inflated by being filled with fluid is attached to the predetermined position on the band 61 by any suitable means. In the figure, the numeral 64 denotes a fluid feed tube made integral with the rigid case 63 to extend through the middle of the upper surface of the rigid case 63, said fluid feed tube 64 having a check valve 65 integral therewith at its outer end projecting outside the rigid case 63, with the filling port (not shown) of the balloon 62 being suitably fixed to the inner end (not shown) extending into the rigid case 63.

Figure 29:
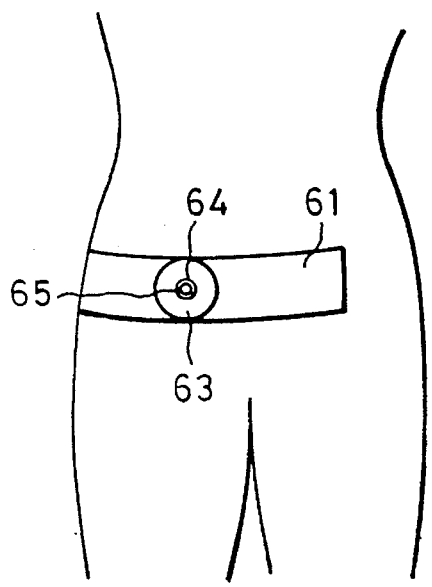
FIG. 29 is a front view of a compressive hemostatic belt according to a fourth embodiment, mounted on an affected part.

According to the compressive hemostatic belt of the invention, as shown in FIG. 29, the rigid case 63 having the balloon 62 received therein is placed on a gauze applied to a catheter insertion wound with the open side of the rigid case directed to the gauze and then the band 61 is stuck to the patient's body. Thereafter, the manual pump and pressure gauge are connected to the fluid feed tube 64. Looking at the pressure gauge, the operator operates the pump to fill the balloon 62 with fluid, whereby the balloon 62 is inflated toward the catheter insertion wound to compress the latter while it is restricted by the rigid case 63 from inflating toward the opposite side.

According to the compressive hemostatic belt of the present invention, the band 61 can be fixed in position by being stuck to the patient's body. This eliminates the prior need of wrapping the band around the body one turn or locking its end by locking means such as a double-coated tape or magic tape; the wrapping of the band around the body is very easy. Further, since the band 61 is intimately contacted with the patient's skin, there is no possibility of the band 61 floating off even if the leg with the band mounted on the thigh or the like is raised. Thus, the fitness of the band 61 is improved, and even if the compressive hemostasis continues for a long time, there is no possibility of causing positional deviation due to wrinkles or twist; thus, effective compressive hemostasis can be attained. Since there is no need to provide locking means, such as a double-coated tape or magic tape, on the end of the band as in the prior art, a single kind of band 61 which is a little shorter can be applied to almost all patients.

The invention is not limited to the above embodiment. For example, in the above embodiment the band 61 has been made entirely of adhesive material but if the adhesive material can be intimately stuck to the patient's body, the band may be made partly of such adhesive material. In this case, there is no need to shave the region around the wound, contributing to labor saving for nurses.

In the above embodiment, the material of the band 61 has been described as a fabric adhesive plaster. However, other adhesive materials than fabric adhesive plaster, such as non-stretchable or low-stretchable textile fabrics, nonwoven fabrics, paper and film may be used.

The compressive hemostatic belt of the present invention is not limited in use to blood vessel catheter examinations but is also applicable to stoppage of bleeding from a wound caused by a catheter treatment, kidney or other dialysis, or an injection using various needles.

As has been described so far, according to the present invention, the band can be intimately contacted with the skin and the mounting on the patient's body is greatly improved, thus achieving labor saving for nurses. Improved fitness on the skin ensures effective compression without positional deviation even if compressive hemostasis continues for a long time. A single kind of band which is a little shorter can be applied to almost all patients.

A fifth embodiment of the present invention will now be described with reference to FIGS. 30 and 31.

Figure 30:
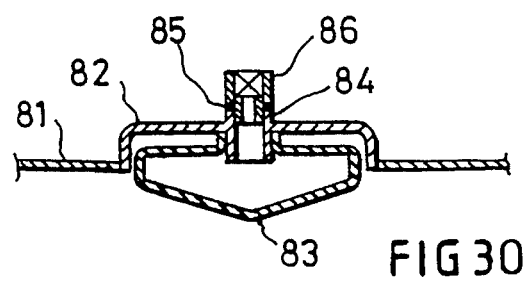
FIG. 30 is a sectional view of the balloon of a compressive hemostatic belt according to a fifth embodiment, with a check valve mounted on said balloon.
Figure 31:
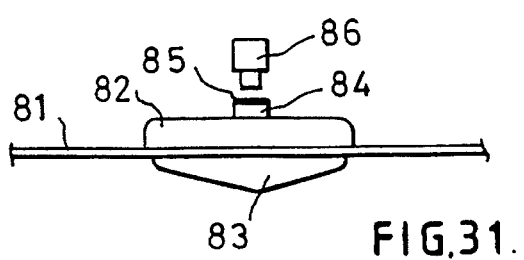
FIG. 31 is a side view of the balloon with the check valve removed therefrom.

FIG. 30 is a principal sectional view of a compressive hemostatic belt, and FIG. 31 is a side view showing the compressive hemostatic belt after use.

In the figures, the numeral 81 denotes a band made of non-stretchable or low-stretchable fiber, nonwoven fabric or film. A rigid case 82 is attached to a predetermined position on the band by any suitable means. The rigid case 82 is made of a rigid material, such as synthetic resin, in bowl form. A balloon 83 adapted to be inflated by being filled with fluid is received in the rigid case 82. The balloon 83 is made of an elastic material, such as rubber, in bag form. The balloon 83 is inflated by being filled with fluid through its opening. The numeral 84 denotes a fluid feed tube made integral with the rigid case 82 to extend through the middle of the upper surface of the rigid case 82. A check valve 86 is removably attached through a seal member such as a packing to the outer end of the fluid feed tube 84 projecting outside the rigid case 82. The opening in the balloon 83 is fixed by any suitable means to the inner end of the fluid feed tube 84 extending into the rigid case 82. The check valve 86 is removably mounted on the outer end of the fluid feed tube 84 by fitted or threaded engagement in such a manner as to prevent leakage of fluid from the balloon 83. A manual pump and a pressure gauge will be connected to the check valve 86 according to the need. Looking at the pressure gauge, the operator operates the pump to fill the balloon 62 with fluid from the check valve 83 through the fluid feed tube 84, thereby inflating the balloon 62. The seal member 85 is interposed between the outer end of the fluid feed tube 84 and the check valve 86 to prevent leakage of fluid from between the outer end of the fluid feed tube 84 and the check valve 86.

With the check valve 86 mounted on the outer end of the fluid feed tube 84 through the seal member 85 by fitted or threaded engagement, the band 81 is wrapped around the part of a patient's body having a catheter insertion wound. Thereafter, fluid is fed from the check valve 86 through the fluid feed tube 84 to the balloon 83 to inflate the latter, thereby compressing the wound. In this connection, leakage of the fluid filled in the balloon 83 is prevented by the seal member 85 and check valve 86 and the pressure in the balloon 83 is maintained for a long time at a value suitable for compressing the wound. In this manner the inflation of the balloon is utilized to effect compression of the wound and when the bleeding from the wound is stopped after the lapse of a predetermined time, the check valve 86 is removed from the outer end of the fluid feed tube 84 as shown in FIG. 31. The rigid case 82 and balloon 83 are discarded, while the check valve 86 alone is recovered. The recovered check valve 86 will be mounted for reuse on the outer end of the fluid feed tube 84 of a fresh compressive hemostatic belt.

In the compressive hemostatic belt of the present invention, the expensive check valve 86 can be removed for repetitive use; thus, the unit cost can be reduced.

In addition, the compressive hemostattc belt of the present invention is not limited in use to blood vessel catheter examinations but is also applicable to stoppage of bleeding from a wound caused by a catheter treatment, kidney or other dialysis, or an injection using various needles.

As has been described so far, according to the present invention, the removable mounting of the check valve enables the check valve to be removed for repetitive use, thus reducing the unit cost to allow the compressive hemostatic belt to be advantageously thrown away after single use.

A sixth embodiment of the invention will now be described with reference to FIGS. 32A through 35.

Figure 32A:
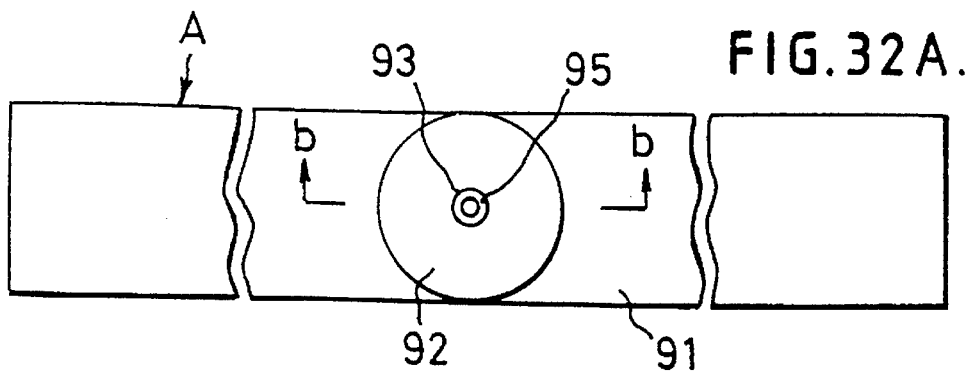
FIG. 32A is a plan view of the compressive hemostatic belt according to the fifth embodiment.
Figure 32B:
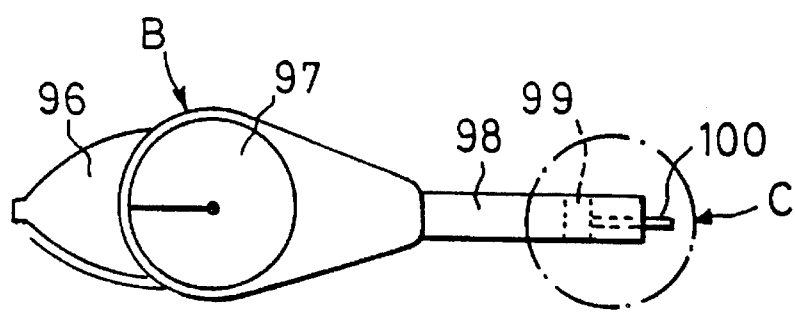
FIG. 32B is a plan view of a pump.
Figure 32C:
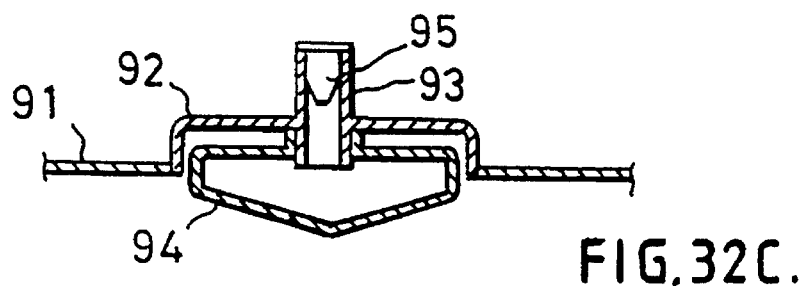
FIG. 32C is a sectional view of a balloon.
Figure 32D:
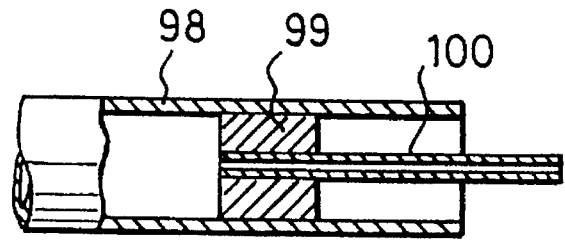
FIG. 32D is a sectional view of the front end of a connecting hose.

FIG. 32A shows a compressive hemostatic belt according to the present invention, and FIG. 32B shows an embodiment of a fluid flow in-and-out pump used therewith. A compressive hemostatic belt A according to the present invention, as in the prior art, has a band 91 made of non-stretchable or low-stretchable fiber, nonwoven fabric or film. A rigid case 92 made of a rigid material such as synthetic resin in bowl form is attached to a predetermined position on the band 91 by any suitable means. A fluid feed tube 93 is made integral with the rigid case 92 to extend through the middle of the upper surface of the rigid case 92. The opening in a balloon 94 made of an elastic material such as rubber in bag form and adapted to be inflated by being filled with fluid is fixed by any suitable means to the inner end of the fluid feed tube 93 extending into the rigid case 92. A check valve 95 is mounted on the outer end of the fluid feed tube 93 projecting outside the rigid case 92 in such a manner as to prevent leakage of the fluid from the balloon 94.

Figures 33A, 33B:
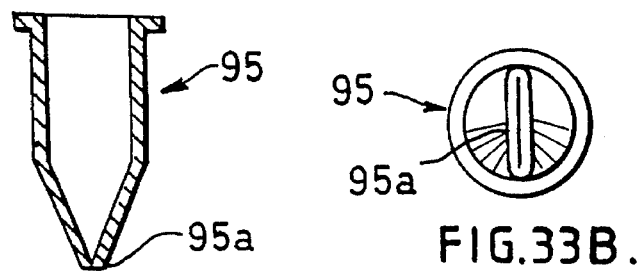
FIG. 33A is a sectional view of a check valve.
FIG. 33B is an end view of the check valve.

The feature of the compressive hemostatic belt A of the present invention which differs from the prior art is the use of the check valve 95 of the construction adapted to effect sealing by internal pressure, such as a duckbill type check valve. This check valve 95, as shown in FIGS. 33A and 33B, has its front end shaped like a duckbill adapted such that the valve portion 95*a* is ordinarily closed by internal pressure and is opened when acted on by an external pressure greater than the internal pressure.

A fluid flow in-and-out pump B, as in the prior art, comprises a pump portion 96 which can be deaerated, a pressure gauge 97 and a connecting hose 98. Looking at the pressure gauge, the operator operates the pump portion 96 to cause fluid to flow in and out through the connecting hose 98.

Figure 34A:
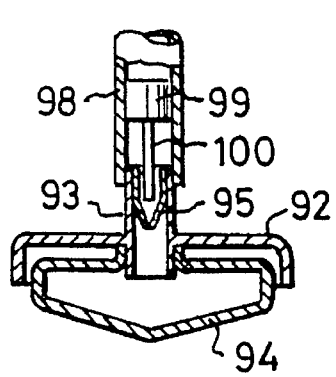
FIGS. 34A through 34C are sectional views of a balloon with a connecting hose being connected, having been connected and removed, respectively.
Figure 34B:
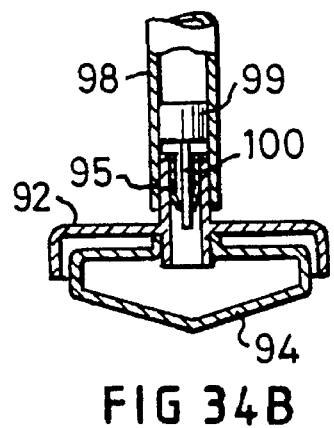

The feature of the fluid flow in-and-out pump B which differs from the prior art is that a plug 99 is tightly fitted in the front end of the connecting hose 98 to close the same and is fixed thereto by a hollow presser pin 100 extending through said plug 99. The length L of the presser pin 100 is such that in the early period of the operation of connecting the connecting hose 98 to the check valve 95, as shown in FIG. 34A, the presser pin 100 does not reach the valve portion 95*a* of the check valve 95 with the valve portion 95*a* remaining closed but that when the connecting hose 98 is connected deeper to the check valve 95, as shown in FIG. 34B, the presser pin 100 reaches the valve portion 95*a* of the check valve 95 to open the valve portion 95*a*.

How to use the compressive hemostatic belt A and the fluid flow in-and-out pump B will now be described.

Figure 34C:
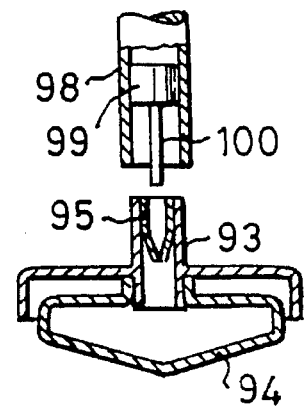

After the compressive hemostatic belt has been wrapped around the part of a patient's body having a catheter insertion wound in the conventional manner, the check valve 95 is connected to the front end of the connecting hose 98 of the fluid flow in-and-out pump B. In the early period of the operation of connecting the connecting hose 98 to the check valve 95, as shown in FIG. 34A, the presser pin 100 does not reach the valve portion 95*a* of the check valve 95 with the check valve 95 remaining closed. When the connecting hose 98 is connected deeper to the check valve 95, as shown in FIG. 34B, the presser pin 100 reaches the valve portion 95*a* of the check valve 95 to open the valve portion 95*a*. This allows fluid to flow in and out. With the check valve 95 allowing fluid to flow in and out, the operator operates the pump portion 96 of the fluid flow in-and-out pump B while looking at the pressure gauge so as to fill the balloon 94 with fluid through the connecting hose 98, presser pin 100 and fluid feed tube 93, thereby inflating the balloon 94. If the balloon 94 is filled with too much fluid, the operator deaerates the balloon while looking at the pressure gauge 97, thereby causing some of the fluid to flow out through the fluid feed tube 93, presser pin 100 and connecting hose 98 to decrease the compressive force until a predetermined pressure is read on the pressure gauge 97, whereupon the deaeration is stopped. Thereafter, the connecting hose 98 of the fluid flow in-and-out pump B is removed from the check valve 95 of the compressive hemostatic belt A, whereupon as shown in FIG. 34C the presser pin 100 is removed from the valve portion 95*a* of the check valve 95 and the check valve 95 is closed by the internal pressure to retain the compressive force of the balloon 94.

In the compressive hemostatic belt A and the fluid flow in-and-out pump B according to the present invention, fluid is allowed to flow in and out with the connecting hose 98 of the fluid flow in-an-out pump B connected to the check valve 95 of the compressive hemostatic belt. When the fluid is to be allowed to flow out of the balloon 94, the compressive force can be ascertained by the pressure gauge, a fact which is convenient for adjusting the compressive force of the balloon 94.

Further, the compressive hemostatic belt according to the invention is simple in the construction of the check valve 95 and hence inexpensive, leading to a decrease in the cost of the compressive hemostatic belt; thus the compressive hemostatic belt of the invention is economically advantageous for throwing away after single use.

Figure 35:
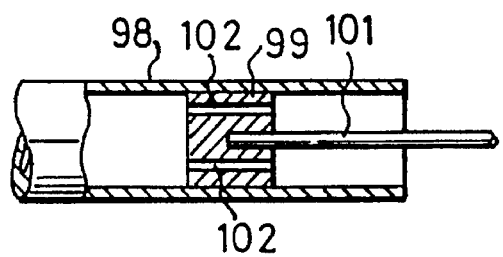
FIG. 35 is a sectional view of the front end of a connecting hose in a different embodiment.

FIG. 35 shows another embodiment of a fluid flow in-and-out pump B according to the present invention. It has a plug 99 tightly fitted in the front end of the connecting hose 98 to close the same and a solid presser pin 101 is provided on said plug 99 to project therefrom, with vent holes 102 formed in the peripheral region of said presser pin 101, the arrangement being such that the valve portion 95*a* of the check valve 95 is opened by the presser pin 101 to open the check valve 95 and in this state the vent holes 102 of the plug 99 are utilized to effect the flow in and out of the fluid.

As has been described so far, according to the present invention, the fluid is allowed to flow in and out with the connecting hose of the fluid flow in-and-out pump connected to the check valve of the compressive hemostatic belt, a fact which is convenient for adjusting the compressive force of the balloon. Further, since the construction of the check valve is simple and inexpensive, the cost of the compressive hemostatic belt can be reduced to the extent that it can be economically advantageously thrown away after single use.

What is claimed is:

1. A compressive hemostatic belt comprising a single band of non-stretchable or low-stretchable fiber, non-woven fabric or film;

a rigid case attached to a predetermined position on one side of said band;

a balloon received in said rigid case adapted to be inflated by being filled with a fluid;

a buckle attaching plate having engaging means on the opposite sides thereof, said buckle attaching plate being rotatably attached to said rigid case on an opposite side of said band; and a pair of buckles attached to opposite ends of said band and engagable with said engaging means of said buckle attaching plate to form a crossed relationship of said band on said rigid case receiving said balloon;

adjacent angles of said crossed relationship of said band being adjustable by rotation of said buckle attaching plate.

2. A compressive hemostatic belt as set forth in claim 1, characterized in that a portion of said band is shaped in curve form having a longitudinal axis lying in a plane of said band curving away from an extension of the longitudinal axis of the remainder of said band.

3. A compressive hemostatic belt as set forth in claim 2, characterized in that portions of the band have cores embedded therein.

4. A compressive hemostatic belt as set forth in claim 2, characterized in that portions of the band are formed of reinforced members.

5. A compressive hemostatic belt as set forth in claim 1, characterized in that said buckle attaching plate has slits in the opposite ends thereof, and each of said buckles can be mounted and dismounted by a single manipulation.

6. A compressive hemostatic belt as set forth in claim 5, characterized in that said buckle attaching plate is attached together with the band to the rigid case having said balloon received therein through a member having a through-hole.

7. A compressive hemostatic belt as set forth in claim 1, characterized in that said buckles are formed with engaging holes, while said buckle attaching plate is provided with engaging members engageable with said engaging holes, said buckles being removably mounted on the buckle attaching plate by utilizing the engagement between said engaging holes and said engaging members.

8. A compressive hemostatic belt as set forth in claim 7, characterized in that said engaging holes and said engaging members are circular in shape.

9. A compressive hemostatic belt as set forth in claim 7, characterized in that said engaging holes and said engaging members are rectangular in shape.

10. A compressive hemostatic belt as set forth in claim 1, characterized in that a predetermined portion of each of the buckles is bifurcated to form a pair of elastic engaging elements having engaging pawls, while said buckle attaching is formed with a pair of grooved frames having insertion grooves for receiving said elastic engaging elements, said frames being spaced a predetermined distance in opposed relation to each other, the arrangement being such that said elastic engaging elements are inserted in the insertion grooves of said grooved frames to engage the engaging pawls of the elastic engaging elements with end edges of the grooved frames so as to removably mount the buckles on the buckle attaching plate.

11. A compressive hemostatic belt as set forth in claim 1, wherein said balloon has a fluid feed tube and a check valve mounted to said tube.

* * * * *